(12) United States Patent (10) Patent No.: US 9,131,745 B2
Peterson et al. (45) Date of Patent: Sep. 15, 2015

(54) FOOTWEAR WITH EMBEDDED TRACKING DEVICE AND METHOD OF MANUFACTURE

(71) Applicants: Ruk Peterson, Endicott, NY (US); Patrick E. Bertagna, Los Angeles, CA (US); Christopher M. Walsh, Pacific Palisades, CA (US)

(72) Inventors: Ruk Peterson, Endicott, NY (US); Patrick E. Bertagna, Los Angeles, CA (US); Christopher M. Walsh, Pacific Palisades, CA (US)

(73) Assignee: GLOBAL TREK XPLORATION CORP., Los Angeles, CA (US)

( * ) Notice: Subject to any disclaimer, the term of this patent is extended or adjusted under 35 U.S.C. 154(b) by 491 days.

(21) Appl. No.: 13/668,874

(22) Filed: Nov. 5, 2012

(65) Prior Publication Data

US 2013/0118039 A1 May 16, 2013

Related U.S. Application Data

(60) Provisional application No. 61/555,861, filed on Nov. 4, 2011.

(51) Int. Cl.
| | |
|---|---|
| *G08B 1/08* | (2006.01) |
| *A43B 3/00* | (2006.01) |
| *A61B 5/00* | (2006.01) |
| *A43B 13/00* | (2006.01) |

(52) U.S. Cl.
CPC .............. *A43B 3/0005* (2013.01); *A43B 3/0015* (2013.01); *A43B 3/0031* (2013.01); *A43B 13/00* (2013.01); *A61B 5/6807* (2013.01)

(58) Field of Classification Search
CPC .... A43B 3/0005; A43B 3/0031; A43B 13/00; A61B 5/1112; A61B 5/6807; G08B 21/0269
USPC ................. 340/539.13, 539.11; 36/136, 75 R
See application file for complete search history.

(56) References Cited

U.S. PATENT DOCUMENTS

| | | | |
|---|---|---|---|
| 5,285,586 A * | 2/1994 | Goldston et al. ................. 36/136 |
| 6,788,200 B1 * | 9/2004 | Jamel et al. .............. 340/539.13 |
| 7,265,666 B2 * | 9/2007 | Daniel ...................... 340/539.11 |
| 7,474,206 B2 * | 1/2009 | Bertagna et al. ......... 340/539.13 |
| 7,920,059 B2 * | 4/2011 | Bertagna et al. ......... 340/539.13 |
| 8,289,156 B2 * | 10/2012 | Bertagna et al. ......... 340/539.13 |
| 8,499,476 B2 * | 8/2013 | Berner et al. .................... 36/136 |
| 8,902,060 B2 * | 12/2014 | Bertagna et al. ......... 340/539.13 |
| 2014/0159951 A1* | 6/2014 | Gou et al. ................ 342/357.25 |

* cited by examiner

*Primary Examiner* — John A Tweel, Jr.
(74) *Attorney, Agent, or Firm* — Larry E. Henneman, Jr.; Gregory P. Gibson; Henneman & Associates, PLC

(57) ABSTRACT

Footwear includes an upper, a sole, a cavity, a location determining device, a wireless communication device, a communication antenna, a first electrical conductor, a location signal antenna, a second electrical conductor, and a bus cable. The cavity is formed in the sole and includes a first portion located on a bottom heel region of the sole and a second portion located on a rear heel region of the sole. The location determining device and the wireless communication device are disposed in the first portion of the cavity. The communication antenna and the location signal antenna are mounted in the second portion of the cavity. The bus cable includes a first end that is electrically coupled to the location determining device and a second end that is mounted in the second portion of the cavity.

28 Claims, 8 Drawing Sheets

FOOTWEAR WITH EMBEDDED TRACKING DEVICE AND METHOD OF MANUFACTURE

RELATED APPLICATIONS

This application claims the benefit of U.S. Provisional Patent Application Ser. No. 61/555,861 entitled "Footwear With Embedded Tracking Device And Method Of Manufacture," filed Nov. 4, 2011 by the same inventors, which is incorporated herein by reference in its entirety.

BACKGROUND OF THE INVENTION

1. Field of the Invention

This invention relates generally to personal tracking devices, and more particularly to a personal tracking device embedded in footwear.

2. Description of the Background Art

Personal tracking devices are known in the art. One possibly desirable means of carrying a personal tracking device is to incorporate the personal tracking device into footwear. However, there are many practical obstacles to incorporating a personal tracking device into footwear, while maintaining the comfort, appearance, and affordability of the footwear.

One issue that must be addressed is the location of the tracking device. If the tracking device (including the antenna) is located in the sole of the footwear, the satellite location determination signals are shielded from the unit by the wearer's foot, and so a relatively sensitive antenna is required. As the sensitivity requirement increases, so generally does the size and cost of the antenna. Additional amplifiers may also be required, which further increases the cost as well as the power consumption of the unit.

Positioning the tracking device in the footwear upper can also be problematic. For example, due to the size of known tracking devices some portion of the upper would need to be significantly expanded in order to accommodate the tracking device. Such an expansion of the upper would almost certainly be noticeable and likely be unacceptable from an appearance standpoint. In addition, the upper typically conforms closely with the foot of the wearer. Therefore, any device of significant size incorporated in the upper might be felt by the wearer, thereby adversely affecting the comfort of the footwear.

Another problem that must be addressed is that the circuitry of the tracking device must be protected from moisture, contamination, and damage, particularly where the footwear is designed for active children and/or outdoor activities such as hunting, wilderness hiking, jogging, and so on. If water gets into the tracking device, the electronic circuitry can short and become nonfunctional. If the tracking device is positioned in the sole of the footwear, the device must be capable of withstanding the weight of the wearer, even when running or jumping.

Another potential problem is that the tracking device may become dislodged from the footwear and lost or damaged. The cost of a tracking device is somewhat significant, and frequent loss of devices would likely pose a barrier to consumer acceptance of the product.

Yet another problem is that the tracking device can interfere with the functionality of the footwear. For example, a large, rigid device in the sole could adversely affect the flexibility of the sole. As another example, a device in the tongue of a shoe could interfere with proper lacing of the shoe.

It can also be a disadvantage if the tracking device is visible or obvious from the outward appearance of the footwear. For example, in the case of a kidnapping it would be a disadvantage if the kidnapper recognized that the victim had footwear with a tracking device, because the kidnapper could frustrate the tracking effort simply by discarding the footwear.

Finally, designs intended to overcome the foregoing problems must be able to withstand the footwear manufacturing process, which can include high temperatures and high pressure pressing operations.

In view of the above-described problems, what is needed is a means for incorporating a tracking device in footwear that does not adversely affect the functionality, the appearance, and/or the comfort of the footwear. What is also needed is a means for incorporating a tracking device in footwear that facilitates the use of relatively inexpensive and/or less sensitive antennas. What is also needed is a means for incorporating a tracking device in footwear that protects the tracking device from moisture, contamination, and physical damage. What is also needed is a means for incorporating a tracking device in footwear that prevents dislodgment and loss of the tracking device. What is also needed is a means for incorporating a tracking device in footwear such that the presence of the tracking device is not apparent from the outward appearance of the footwear. What is also needed is a footwear manufacturing process that facilitates incorporation of a tracking device into the footwear.

SUMMARY

The present invention overcomes the problems associated with the prior art by providing footwear with an embedded tracking device and a method of manufacturing the footwear.

Example footwear includes an upper, a sole, a cavity, a location determining device, a wireless communication device, a communication antenna, a first electrical conductor, a location signal antenna, a second electrical conductor, and a bus cable. The upper includes a bottom heel region and a rear heel region. The sole includes a bottom heel region and a rear heel region. The bottom heel region of the sole is coupled to the bottom heel region of the upper, and the rear heel region of the sole is coupled to the rear heel region of the upper. The cavity is formed in the sole and includes a first portion and a second portion. The first portion of the cavity is located on the bottom heel region of the sole and the second portion of the cavity is located on the rear heel region of the sole. The location determining device is disposed in the first portion of the cavity, and the wireless communication device is electronically coupled to the location determining device. The communication antenna is mounted in the second portion of the cavity and is electrically coupled to the wireless communication device via the first electrical conductor. The location signal antenna is mounted in the second portion of the cavity, and is electrically coupled to the location determining device via the second electrical conductor. The bus cable includes a first end that is electrically coupled to the location determining device and a second end that is mounted in the second portion of the cavity.

In an example embodiment, the sole includes a heel counter support and a midsole. The rear heel region of the sole is part of the heel counter support and the bottom heel region of the sole is part of the midsole. In a more particular embodiment, the heel counter support and the midsole are individual elements permanently bonded to one another. Alternatively, the heel counter support and the midsole are formed as integral parts of the sole.

In another example embodiment, the bus cable is a universal serial bus cable having a female receptacle, the rear heel region defines an opening through which the second portion of the cavity is accessible from outside the footwear, the female receptacle of the universal serial bus cable is disposed in the second portion of the cavity; and the female receptacle is aligned with the opening. In a more particular embodiment, the communication antenna is a global system for mobile antenna and the location signal antenna is a global positioning system antenna. In another more particular embodiment, the footwear further includes a rechargeable battery disposed in the first portion of the cavity and electrically coupled to the universal serial bus.

In another example embodiment, at least a portion of the second portion of the cavity is defined by a contoured interior wall, the communication antenna includes a flexible substrate, and the flexible substrate is adhered to the contoured wall.

In yet another example embodiment, the location determining device and the wireless communication device are integral parts of a tracking device. In a more particular example, the tracking device includes a housing, the location determining device and the wireless communication device are disposed in the housing, and the housing is disposed in the first portion of the cavity. In an even more particular embodiment, the bus cable is a universal serial bus cable, the communication antenna is a global system for mobile antenna, and the location signal antenna is a global positioning system antenna.

In another example embodiment, the footwear further includes a cover plate that is adapted to mount over the first portion of the cavity between the bottom heel portion of the sole and the bottom heel portion of the upper.

A method for manufacturing footwear is also described. The method includes the steps of providing a sole having a bottom heel region defining a first portion of a cavity and a rear heel region defining a second portion of a cavity, providing a location determining device, providing a location signal antenna, and electrically coupling the location signal antenna to the location determining device. The example method additionally includes providing a wireless communication device, providing a communication antenna, and electrically coupling the communication antenna to the wireless communication device. The example method additionally includes providing a bus cable having a first end and a second end and electrically coupling the first end of the bus cable to at least one of the location determining device and the wireless communication device. The example method additionally includes positioning the location determining device and the wireless communication device in the first portion of the cavity and mounting the location signal antenna, the communication antenna, and the second end of the bus cable in the second portion of the cavity. The method additionally includes providing an upper having a bottom heel region and a rear heel region, coupling the bottom heel region of the upper to the bottom heel region of the sole, and coupling the rear heel region of the upper to the rear heel region of the sole.

In a more particular example method, the sole includes a heel counter support and a midsole. The rear heel region of the sole is part of said heel counter support and the bottom heel region of the sole is part of the midsole. In a more particular method, the step of providing the heel includes providing a heel counter support, providing a midsole, and fastening the heel counter support to the midsole. In another more particular method, the step of providing the sole includes forming the heel counter support and the midsole as integral parts of the sole.

In another more particular example method, the step of providing the bus cable includes providing a universal serial bus cable, wherein the second end of the bus cable is a female receptacle of the universal serial bus cable. The step of providing the sole includes forming an opening in the rear heel region of the sole, so that the cavity is accessible from outside the footwear via the opening, and the step of mounting the second end of the bus cable in the second portion of the cavity includes aligning the female receptacle with the opening. In an even more particular method, the communication antenna is a global system for mobile antenna and the location signal antenna is a global positioning system antenna. Another more particular method includes providing a rechargeable battery, electrically coupling the rechargeable battery to the bus cable, and positioning the rechargeable battery in the first portion of the cavity.

In another particular example method, at least a portion of the second portion of the cavity is defined by a contoured interior wall, the communication antenna includes a flexible substrate, and the flexible substrate is adhered to the contoured wall.

In another particular example method, the location determining device and the wireless communication device are integral parts of a tracking device. In a more particular example method, the tracking device includes a housing, the location determining device and the wireless communication device are disposed in the housing, and the housing is disposed in the first portion of the cavity. In an even more particular example method, the step of providing the bus cable includes providing a universal serial bus cable, the step of providing a communication antenna includes providing a global system for mobile antenna, and the step of providing the location signal antenna includes providing a global positioning system antenna.

Another particular example method further includes providing a cover plate and mounting the cover plate over the first portion of the cavity between the bottom heel portion of the sole and the bottom heel portion of the upper.

BRIEF DESCRIPTION OF THE DRAWINGS

The present invention is described with reference to the following drawings, wherein like reference numbers denote substantially similar elements.

DETAILED DESCRIPTION

The present invention overcomes the problems associated with the prior art, by providing footwear with an embedded tracking device. In the following description, numerous specific details are set forth (e.g., particular electronic components) in order to provide a thorough understanding of the invention. Those skilled in the art will recognize, however, that the invention may be practiced apart from these specific details. In other instances, details of well known footwear manufacturing and electronics assembly practices and components have been omitted, so as not to unnecessarily obscure the present invention.

Figure 1:
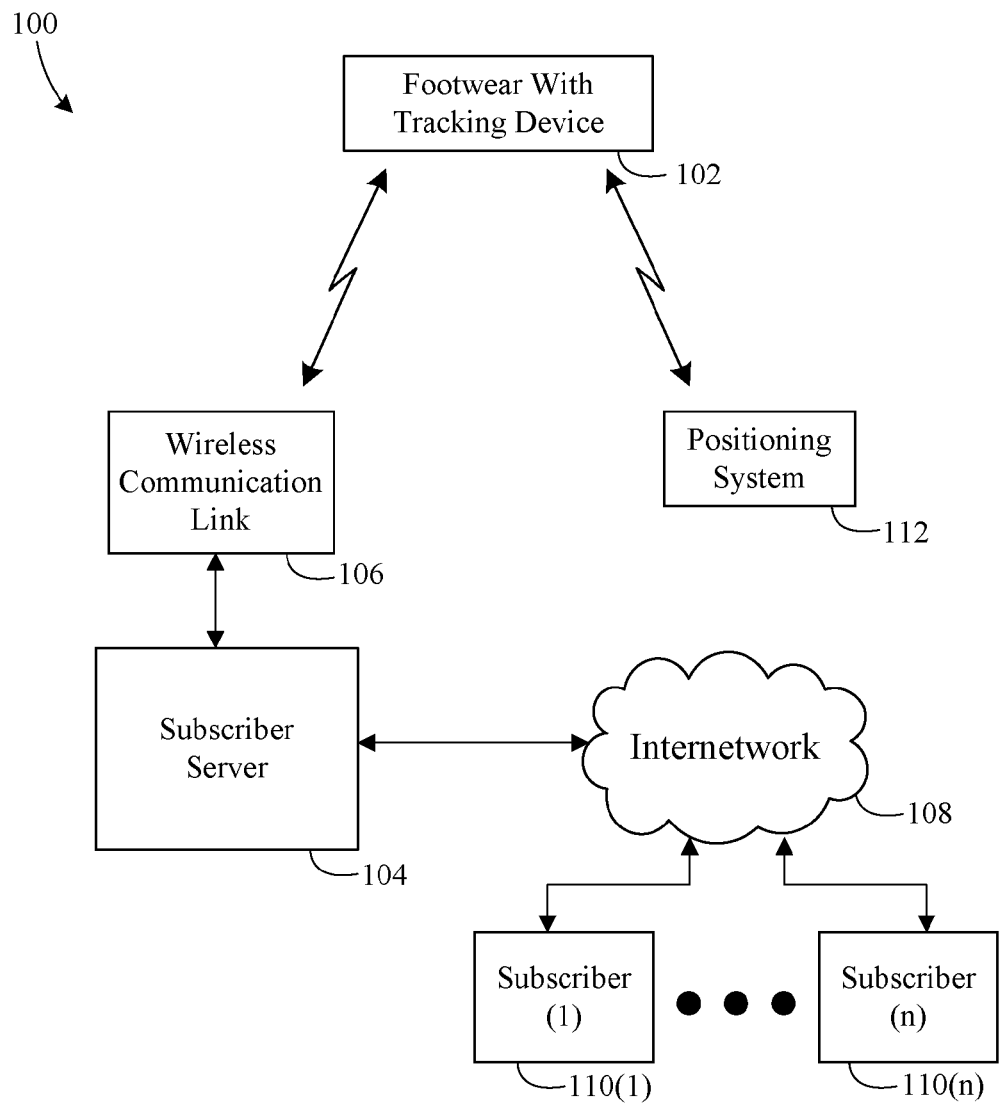
FIG. 1 is a block diagram of a tracking system.

FIG. 1 is a block diagram of a tracking system 100 including the footwear 102 of the present invention. Tracking system 100 further includes a subscriber server 104, a wireless communication link 106, an internetwork 108, one or more subscribers 110(1-n), and a positioning system 112.

Footwear 102 includes a tracking device that communicates wirelessly with subscriber server 104 via wireless communication link 106. In the particular embodiment described, wireless communications link 106 is a mobile telephone network. However, the invention is not limited to use with any particular type of mobile telephone network. Indeed, wireless communication link 106 represents any means of wireless communication, now known or yet to be discovered, that facilitates communication between footwear 102 and subscriber server 104 including, but not limited to cellular networks (e.g., CDMA and GSM), satellite networks, WIFI networks, and radio communication.

Subscriber server 104 receives data from footwear 102 indicative of the geographic position of footwear 102, and provides the information to subscribers 110(1-n) via internetwork 108. In this particular embodiment of the invention, internetwork 108 is the Internet. However, any suitable means of communication between subscriber server 104 and subscriber servers 110(1-n) can be used for internetwork 108.

Subscribers 110(1-n) represent individuals with an interest in the location of the person wearing footwear 102. For example tracking system 100 can be used by parents to locate children, by service departments to locate emergency service personnel in the field, and so on. Subscribers 110(1-n) communicate with subscriber server 104 via internetwork 108 using some sort of client device including, but not limited to, a personal computer, a telephone, and so on.

Responsive to a command from subscriber server 104, footwear 102 determines its location using location signals received from positioning system 112 and transmits data indicative of the determined system back to subscriber server 104. Positioning system 112 represents any type of satellite or terrestrial based positioning system that transmits signals that can be used to determine location. For example, a global positioning system (GPS) currently in use employs a plurality of satellites that continuously transmit signals. GPS receivers can calculate location by determining the difference in the time of receipt of signals from different satellites. GPS technology is well known, and so will not be described in detail herein.

As an alternative to a GPS type system, positioning system 112 can be incorporated into wireless communication link 106. For example, wireless telephone networks now have the capability of determining the location of mobile telephone handsets based on signals from a plurality of signal towers in the network. Wireless communication link 106 can then provide the determined location directly to footwear 102, which in turn can communicate the location to subscriber server 104. As a result, positioning system 112 can be thought of as either optional or as being incorporated into wireless communication link 106.

Figure 2:
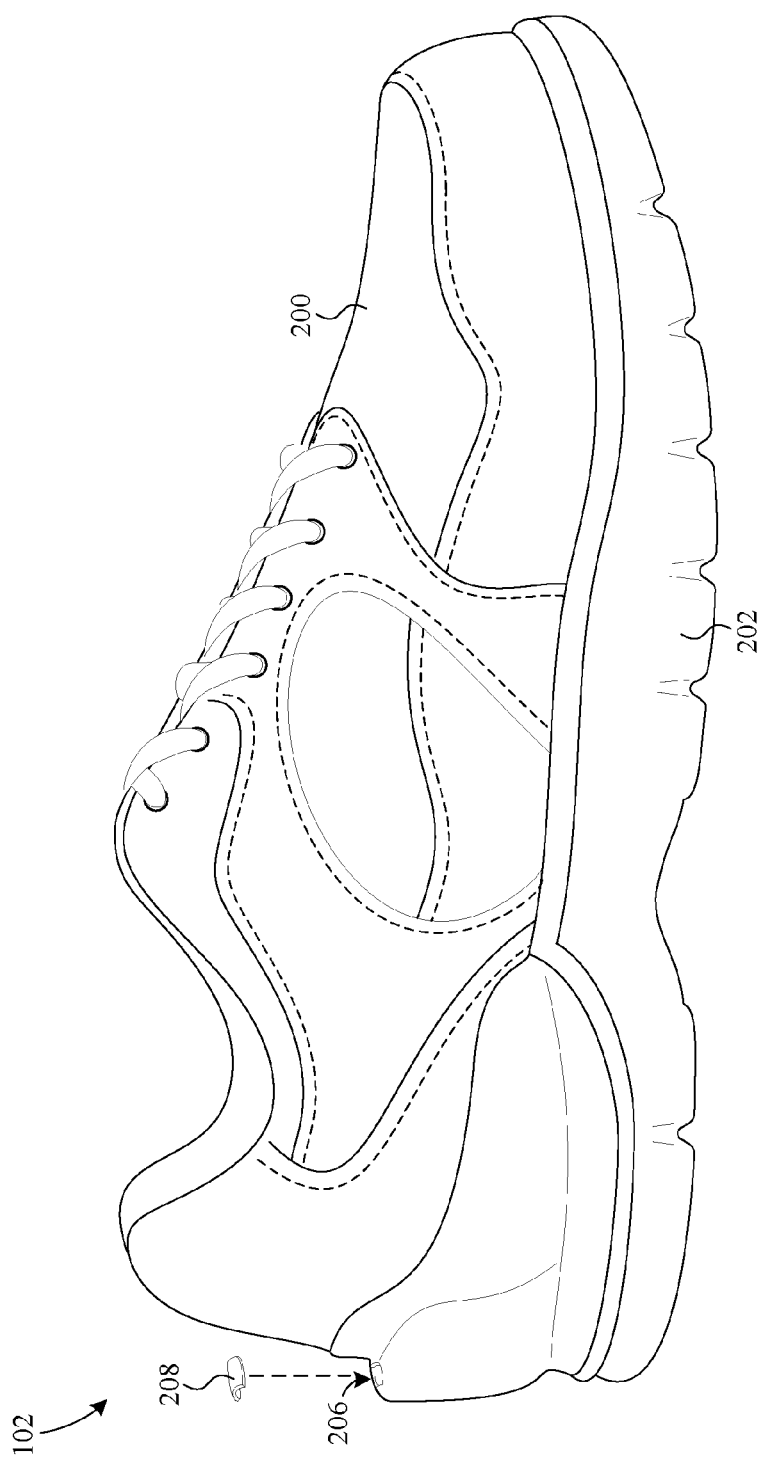
FIG. 2 is a side view of footwear with an embedded tracking system for use with the tracking system of FIG. 1.

FIG. 2 is a side view of footwear 102 according to one example embodiment of the present invention. Footwear 102 includes an upper 200, a sole 202, and a tracking device 204 (shown in FIG. 3). Upper 200 is attached to sole 202 and tracking device 204 is disposed therebetween. A bus receptacle 206 located on sole 202 facilitates electrical charging of tracking device 204 and data communication to and from an external device (e.g., computer). Apart from bus receptacle 206, tracking device 204 is not visible in the view of FIG. 2. The concealment of the tracking device provides an advantage in that a kidnapper would not be alerted to the fact that he/she might be being tracked. When not in use, bus receptacle 206 is covered by a resilient plug 208 that protects against dirt and water entering connector 202. Note that plug 208 is only shown completely detached from footwear 102 to provide a better view of receptacle 206. Indeed, plug 208 is ordinarily attached to sole 202 to prevent it from being misplaced or lost during normal use.

Figure 3:
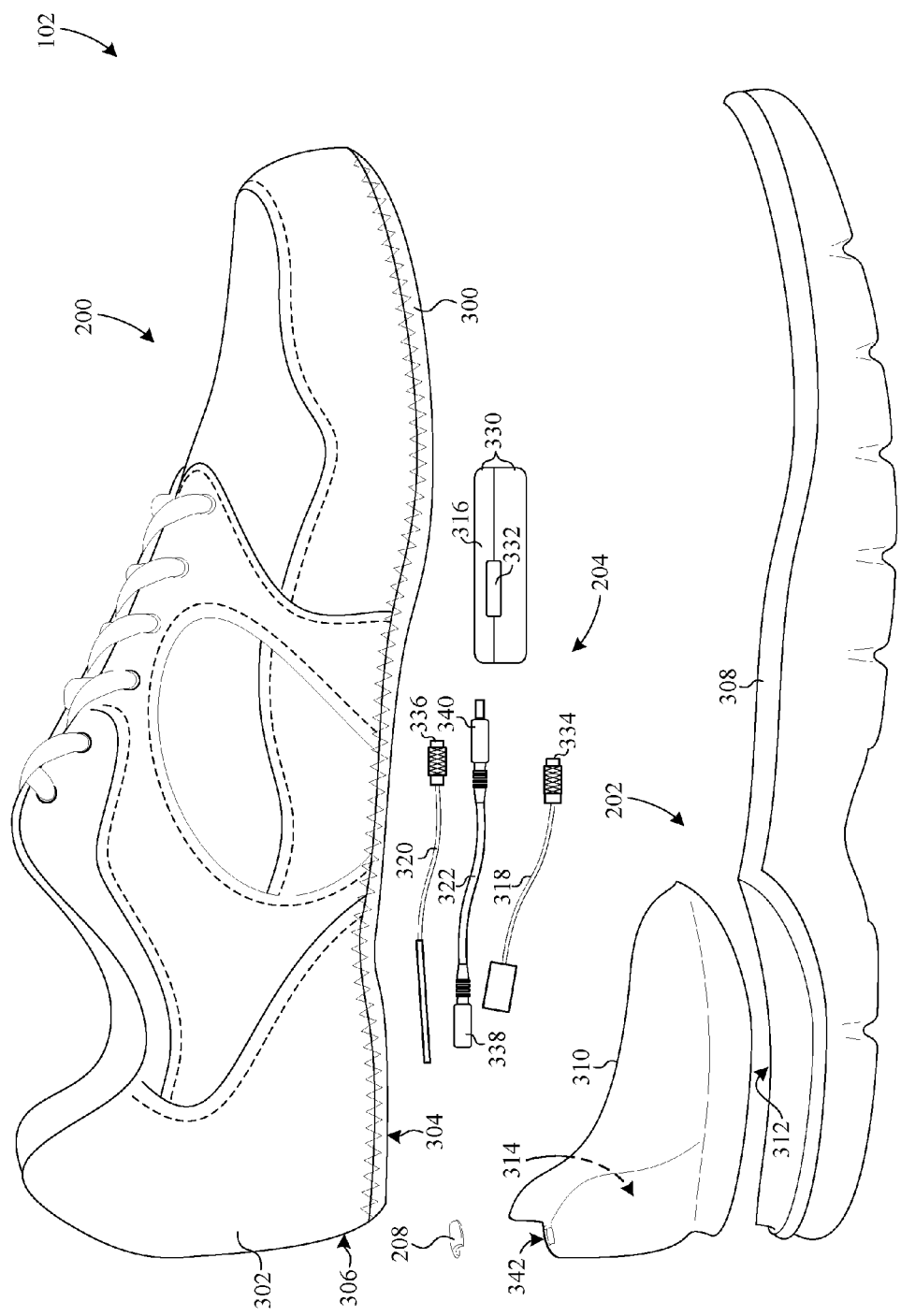
FIG. 3 is an exploded side view of the footwear of FIG. 2.

FIG. 3 is an exploded side view of footwear 102. Upper 200 includes an insole 300 coupled to a counter 302. Insole 300 and counter 302 define a bottom heel region 304 and a rear heel region 306, respectively, of upper 200.

Sole 202 includes a midsole 308 and a heel counter support 310. Midsole 308 and heel counter support 310 define a bottom heel region 312 and a rear heel region 314, respectively, of sole 202. In the example embodiment, midsole 308 and heel counter support 310 are formed separately and then bonded together by some suitable means such as, for example, adhesive. Alternatively, sole 202 could be a single body wherein counter support 310 is an integral feature of midsole 308.

Tracking device 204 includes an electronics module 316, a location signal antenna 318, a wireless communication antenna 320, and a bus cable 322. Electronics module 316 includes a location determining device 324 (shown in FIG. 5), a wireless communication device 326 (shown in FIG. 5), and a battery 328 (shown in FIG. 5) disposed within a housing 330. In the example embodiment, location determining device 324 is a global positioning system device and wireless communication device 326 is a wireless cellular modem. Battery 328 is, for example, a lithium polymer cell that is rechargeable via connecting a USB charger to receptacle 206. Electronics module 316 further includes a user input 332 for inputting user commands such as, for example, during factory programming operations. In the example embodiment, location signal antenna 318 is a GPS antenna and wireless communication antenna 320 is a global system for mobile (GSM) antenna. Antennas 318, 320, and bus cable 322 are both disposed in the heel portion of sole 202 of footwear 102. Antenna 318 is a passive, directional antenna that is adapted to mount in an upwardly facing position inside of counter support 310. In this position, GPS satellite signals are not blocked by the foot of the wearer. At the opposite end, antenna 318 includes a microminiature coaxial (MMCX) connector 334 that electrically connects to module 316. Antenna 320 is formed on a flexible substrate that is adapted to adhere to the contoured interior of counter support 310. The opposite end of antenna 320 also includes a MMCX connector 336 that electrically connects to module 316. In the example embodiment, bus cable 322 is a universal serial bus cable (e.g., micro USB cable, mini USB cable, etc.) having a female end 338 and a male end 340. Female end 338 mounts in counter support 310 and is aligned with an opening 342 formed therethrough so as to, together, form receptacle 206. Male end 340 electrically connects to module 316.

Figure 4:
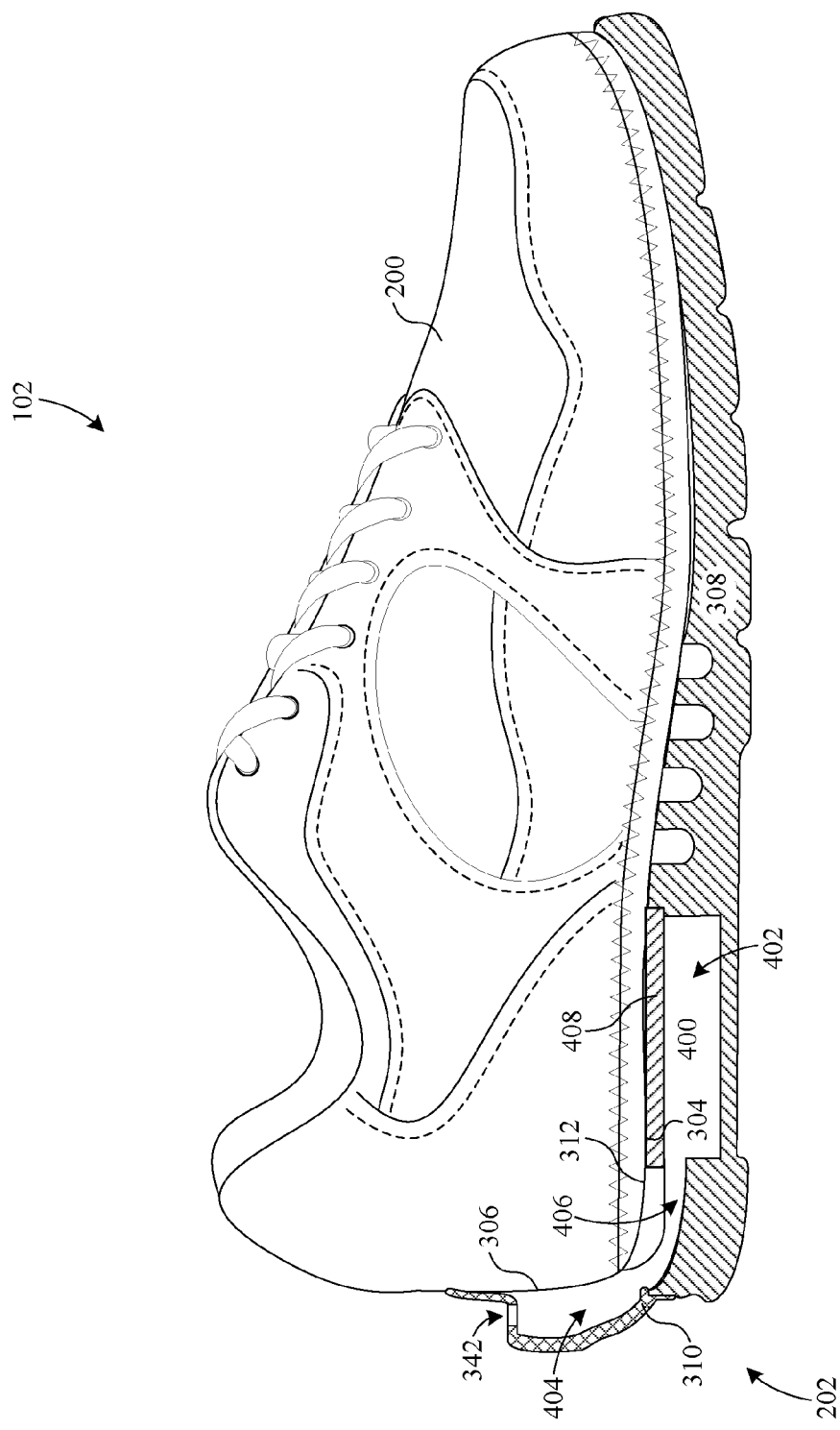
FIG. 4 is a partially sectioned side view of the footwear of FIG. 2.

FIG. 4 is a side view of footwear 102 showing sole 202 sectioned and tracking device 204 removed. As shown, sole 202 defines a cavity 400 having a first portion 402 and a second portion 404, which are defined by midsole 308 and counter support 310, respectively. First portion 402 and second portion 404 are connected via a channel 406 formed therebetween. Cavity 400 is adapted to receive tracking device 204. More specifically, first portion 402 is adapted to receive module 316 and second portion 404 is adapted to receive location signal antenna 318, wireless communication antenna 320, and bus cable 322. Location signal antenna 318, wireless communication antenna 320, and bus cable 322 are routed to module 316 through channel 406. Sole 202 further includes a cover plate 408 that mounts over first portion 402 of cavity 400 and is part of bottom heel region 312.

Figure 5:
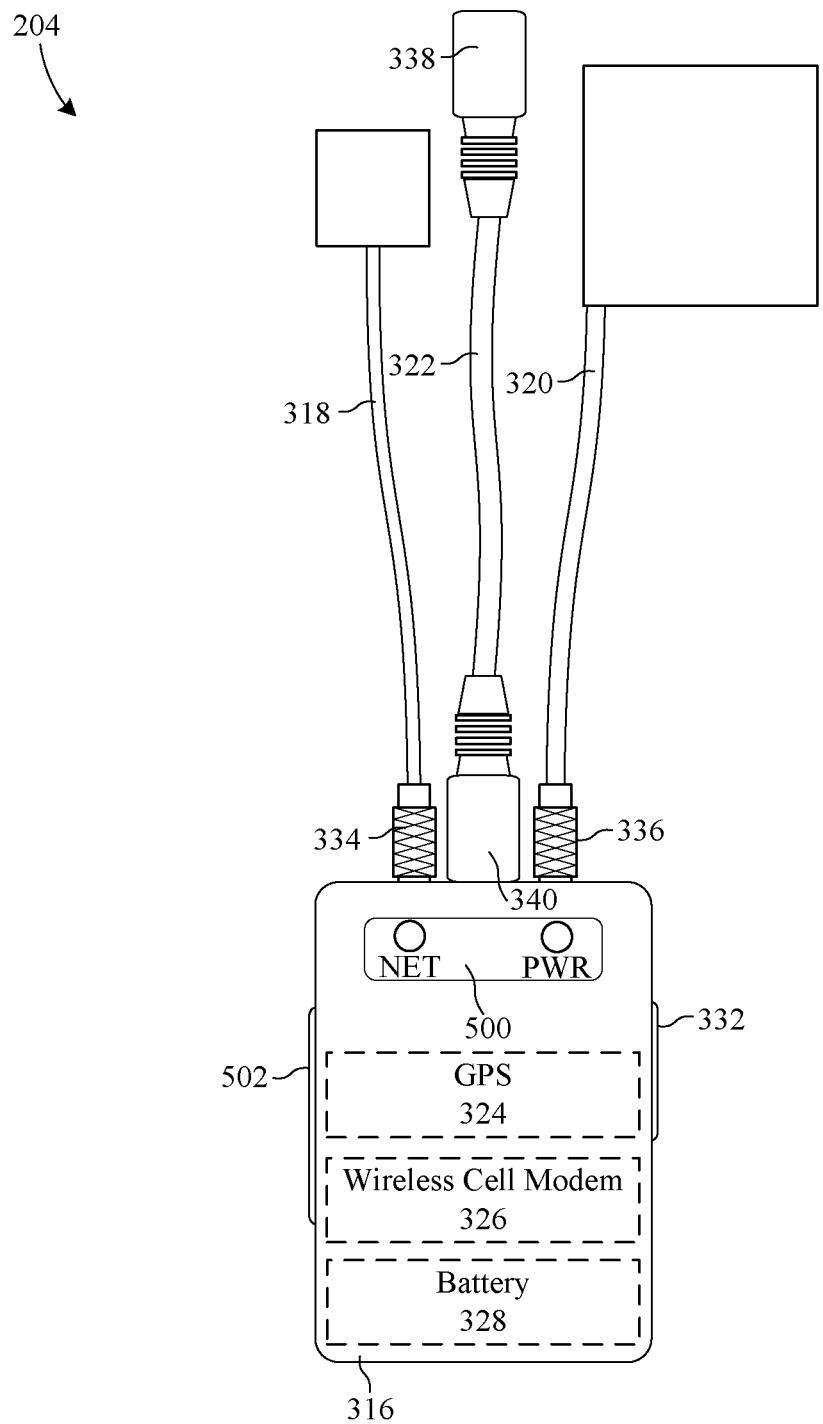
FIG. 5 is a top view of a tracking device of the footwear of FIG. 2.

FIG. 5 is a top view of tracking device 204 wherein antenna 318, antenna 320, and bus cable 322 are plugged into module 316. Module 316 further includes an LED panel 500, identification card (e.g., SIM card) slot 502. Although not visible, module 316 includes a set of MMCX jacks connected to MMCX connectors 334 and 336. Furthermore, module 316 also includes a female USB receptacle connected to male end 340 of cable 322.

Figure 6:
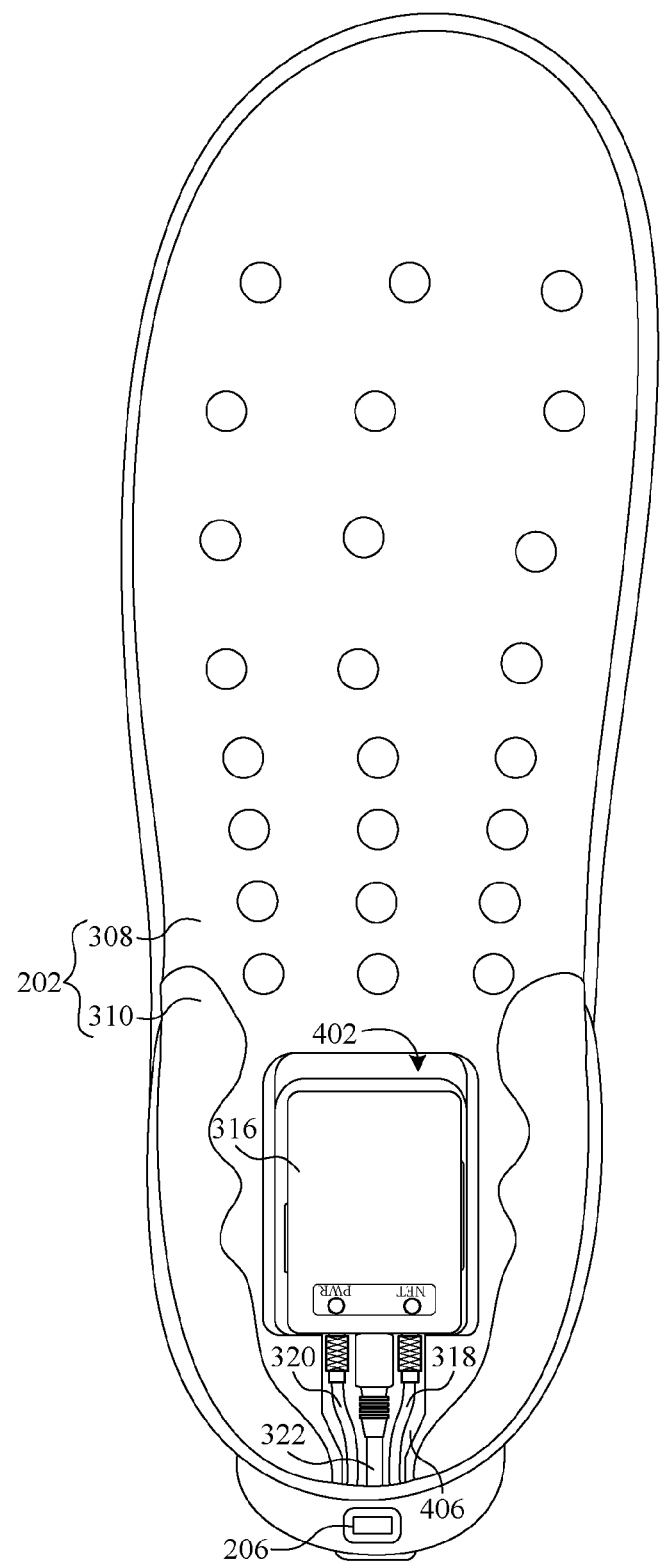
FIG. 6 is a top view of the footwear of FIG. 2 shown with the upper removed.

FIG. 6 is a top view of tracking device 204 seated in cavity 400 of sole 202. That is, module 316 is seated in first portion 402 of cavity 400. Additionally, antenna 318, antenna 320, and bus cable 322 are routed through channel 406 and mounted in second portion 404 of cavity 200.

Figure 7:
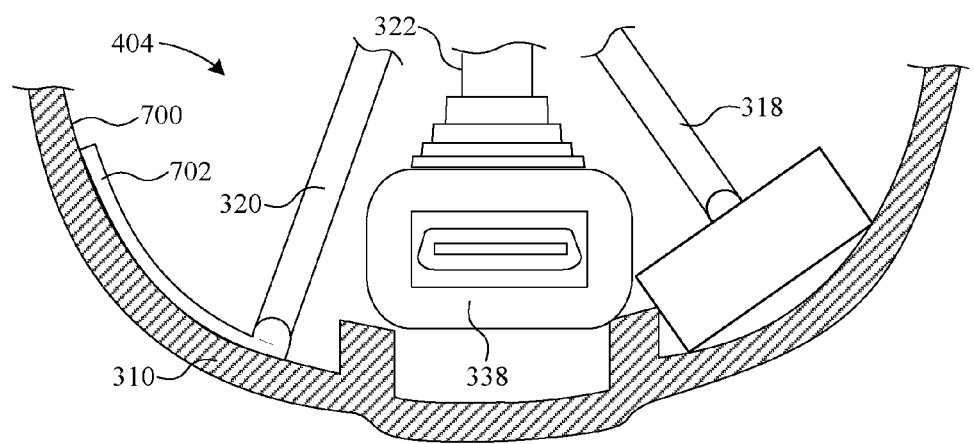
FIG. 7 is a top sectioned view of a counter support of the footwear of FIG. 2.

FIG. 7 is a top sectioned view of counter support 310 wherein antenna 318, antenna 320, and bus cable 322 are mounted in second portion 404 of cavity 400. As shown, second portion 404 of cavity 400 is defined by an interior surface 700 of counter support 310. In the example embodiment, antenna 318 and female end 336 of bus cable 322 are mounted via the physical features of counter support 310 that are defined by interior surface 700. Antenna 320 includes a flexible substrate 702 that is fixed to interior surface 700 via an adhesive.

Figure 8:
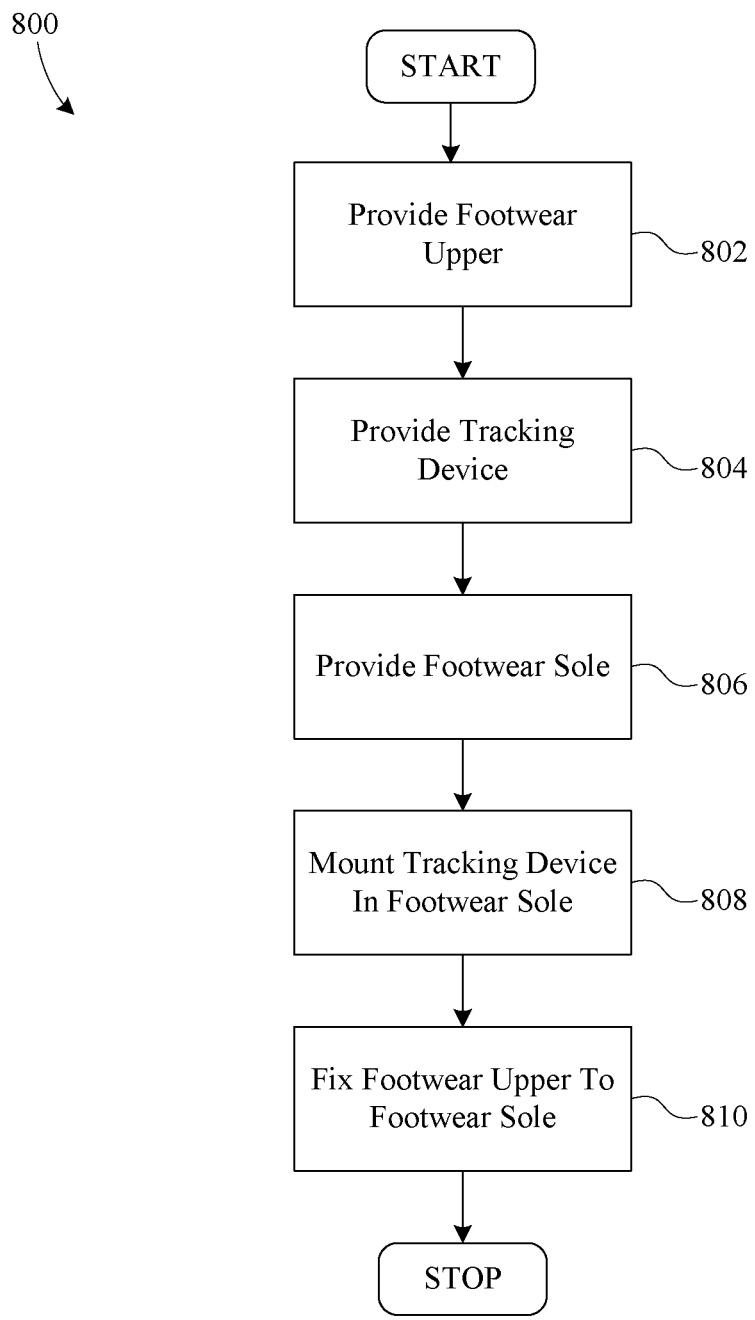
FIG. 8 is a flow chart summarizing one method for manufacturing footwear with an embedded tracking device.

FIG. 8 is a flow chart 800 summarizing a method for manufacturing footwear. In a first step 802, a footwear upper is provided. Then, in a second step 804, a tracking device is provided. Next, in a third step 806, a footwear sole is provided. Then, in a fourth step 808, the tracking device is mounted in the footwear sole. Finally, in a fifth step 810, the footwear upper is fixed to the footwear sole.

The description of particular embodiments of the present invention is now complete. Many of the described features may be substituted, altered or omitted without departing from the scope of the invention. For example, if the wireless communication device 326 can obtain position information from the particular wireless communication link 106 used, then the GPS components (location determining device 324 and antenna 318) can be omitted. As another example, different types of cables (e.g., micro USB, mini USB, etc.) may be substituted for bus cable 322. These and other deviations from the particular embodiments shown will be apparent to those skilled in the art, particularly in view of the foregoing disclosure. The description of particular embodiments of the present invention is now complete. Many of the described features may be substituted, altered or omitted without departing from the scope of the invention.

We claim:

1. Footwear comprising:
   an upper having a bottom heel region and a rear heel region;
   a sole having a bottom heel region and a rear heel region, said bottom heel region of said sole being coupled to said bottom heel region of said upper, said rear heel region of said sole being coupled to said rear heel region of said upper;
   a cavity formed in said sole, said cavity having a first portion and a second portion, said first portion being located on said bottom heel region of said sole and said second portion being located on said rear heel region of said sole;
   a location determining device disposed in said first portion of said cavity;
   a wireless communication device electronically coupled to said location determining device;
   a communication antenna mounted in said second portion of said cavity;
   a first electrical conductor, said communication antenna being electrically coupled to said wireless communication device via said first electrical conductor;
   a location signal antenna mounted in said second portion of said cavity;
   a second electrical conductor, said location signal antenna being electrically coupled to said location determining device via said second electrical conductor; and
   a bus cable disposed in said cavity, said bus cable having a first end electrically coupled to said location determining device and a second end mounted in said second portion of said cavity.

2. Footwear according to claim 1, wherein said sole includes a heel counter support and a midsole, said rear heel region of said sole being part of said heel counter support, said bottom heel region of said sole being part of said midsole.

3. Footwear according to claim 2, wherein said heel counter support and said midsole are individual elements permanently bonded to one another.

4. Footwear according to claim 2, wherein said heel counter support and said midsole are formed as integral parts of said sole.

5. Footwear according to claim 1, wherein:
   said bus cable is a universal serial bus cable having a having a female receptacle;
   said rear heel region defines an opening through which said second portion of said cavity is accessible from outside said footwear;
   said female receptacle of said universal serial bus cable is disposed in said second portion of said cavity; and
   said female receptacle is aligned with said opening.

6. Footwear according to claim 5, wherein said communication antenna is a global system for mobile antenna, and said location signal antenna is a global positioning system antenna.

7. Footwear according to claim 5, further comprising a rechargeable battery disposed in said first portion of said cavity, said researchable battery being electrically coupled to said universal serial bus.

8. Footwear according to claim 1, wherein said communication antenna is a global system for mobile antenna.

9. Footwear according to claim 1, wherein:
   at least a portion of said second portion of said cavity is defined by a contoured interior wall;
   said communication antenna includes a flexible substrate; and
   said flexible substrate is adhered to said contoured wall.

10. Footwear according to claim 1, wherein said location signal antenna is a global positioning system antenna.

11. Footwear according to claim 1, wherein said location determining device and said wireless communication device are integral parts of a tracking device.

12. Footwear according to claim 11, wherein said tracking device includes a housing, said location determining device and said wireless communication device being disposed in said housing, said housing being disposed in said first portion of said cavity.

13. Footwear according to claim 12, wherein:
   said bus cable is a universal serial bus cable;
   said communication antenna is a global system for mobile antenna; and
   said location signal antenna is a global positioning system antenna.

14. Footwear according to claim 1, further comprising cover plate adapted to mount over said first portion of said cavity between said bottom heel portion of said sole and said bottom heel portion of said upper.

15. A method for manufacturing footwear, said method comprising:
   providing a sole having a bottom heel region and a rear heel region, said step of providing said sole further comprising forming a first portion of a cavity on said bottom heel region of said sole, said step of providing said sole further comprising forming a second portion of said cavity on said rear heel region of said sole;
   providing a location determining device;
   providing location signal antenna;
   electrically coupling said location signal antenna to said location determining device;
   providing a wireless communication device;
   providing a communication antenna;
   electrically coupling said communication antenna to said wireless communication device;
   providing a bus cable having a first end and a second end;
   electrically coupling said first end of said bus cable to at least one of said location determining device and said wireless communication device;
   positioning said location determining device in said first portion of said cavity;
   positioning said wireless communication device in said first portion of said cavity;
   mounting said location signal antenna in said second portion of said cavity;
   mounting said communication antenna in said second portion of said cavity;
   mounting said second end of said bus cable in said second portion of said cavity;
   providing an upper having a bottom heel region and a rear heel region;
   coupling said bottom heel region of said upper to said bottom heel region of said sole; and
   coupling said rear heel region of said upper to said rear heel region of said sole.

16. A method for manufacturing footwear according to claim 15, wherein said sole includes a heel counter support and a midsole, said rear heel region of said sole being part of said heel counter support, said bottom heel region of said sole being part of said midsole.

17. A method for manufacturing footwear according to claim 16, wherein said step of said heel includes:
   providing heel counter support;
   providing a midsole; and
   fastening said heel counter support to said midsole.

18. A method for manufacturing footwear according to claim 16, wherein said step of providing said sole includes forming said heel counter support and said midsole as integral parts of said sole.

19. A method for manufacturing footwear according to claim 15, wherein:
   said step of providing said bus cable includes providing a universal serial bus cable, said second end of said bus cable being a female receptacle of said universal serial bus cable;
   said step of providing said sole includes forming an opening in said rear heel region of said sole, said cavity being accessible from outside said footwear via said opening; and
   said step of mounting said second end of said bus cable in said second portion of said cavity includes aligning said female receptacle with said opening.

20. A method for manufacturing footwear according to claim 19, wherein said communication antenna is a global system for mobile antenna, and said location signal antenna is a global positioning system antenna.

21. A method for manufacturing footwear according to claim 19, further comprising:
   providing a rechargeable battery;
   electrically coupling said rechargeable battery to said bus cable; and
   positioning said rechargeable battery in said first portion of said cavity.

22. A method for manufacturing footwear according to claim 15, wherein said communication antenna is a global system for mobile antenna.

23. A method for manufacturing footwear according to claim 15, wherein:
   at least a portion of said second portion of said cavity is defined by a contoured interior wall;
   said communication antenna includes a flexible substrate; and
   said flexible substrate is adhered to said contoured wall.

24. A method for manufacturing footwear according to claim 15, wherein said location signal antenna is a global positioning system antenna.

25. A method for manufacturing footwear according to claim 15, wherein said location determining device and said wireless communication device are integral parts of a tracking device.

26. A method for manufacturing footwear according to claim 25, wherein said tracking device includes a housing, said location determining device and said wireless communication device being disposed in said housing, said housing being disposed in said first portion of said cavity.

27. A method for manufacturing footwear according to claim 26, wherein:
   said step of providing said bus cable includes providing a universal serial bus cable;
   said step of providing a communication antenna includes providing a global system for mobile antenna; and
   said step of providing said location signal antenna includes providing a global positioning system antenna.

28. A method for manufacturing footwear according to claim 15, further comprising providing a cover plate and mounting said cover plate over said first portion of said cavity between said bottom heel portion of said sole and said bottom heel portion of said upper.

* * * * *